(12) United States Patent
Rios Vasquez et al.

(10) Patent No.: US 9,145,352 B2
(45) Date of Patent: Sep. 29, 2015

(54) QUATERNARY N-(HALOMETHYL) AMMONIUM SALTS AS THERAPEUTIC AGENTS

(75) Inventors: Luz Amalia Rios Vasquez, Manizales (CO); Rogelio Ocampo Cardona, Manizales (CO); Sandra Milena Duque, Manizales (CO); Sara Maria Robledo Restrepo, Medellin (CO); Ivan Dario Velez Bernal, Medellin (CO); David Leonardo Cedeño Medina, Normal, IL (US); Marjorie Ann Jones, Carlock, IL (US)

(73) Assignees: UNIVERSIDAD DE CALDAS, Caldas (CO); UNIVERSIDAD DE ANTIOQUIA, Antioquia (CO); THE BOARD OF TRUSTEES OF ILLINOIS STATE UNIVERSITY, Normal, IL (US)

( * ) Notice: Subject to any disclaimer, the term of this patent is extended or adjusted under 35 U.S.C. 154(b) by 371 days.

(21) Appl. No.: 13/484,233

(22) Filed: May 30, 2012

(65) Prior Publication Data

US 2014/0194640 A1    Jul. 10, 2014

(51) Int. Cl.
 *C07C 211/63* (2006.01)
 *C07F 7/10* (2006.01)
 *A61K 31/14* (2006.01)
(52) U.S. Cl.
 CPC .............. *C07C 211/63* (2013.01); *A61K 31/14* (2013.01); *C07F 7/10* (2013.01)

(58) Field of Classification Search
 CPC .......... C07C 211/63; C07F 7/10; A61K 31/14
 USPC ...................... 564/291, 8; 556/413
 See application file for complete search history.

(56) References Cited

FOREIGN PATENT DOCUMENTS

GB            788915      *   1/1958

OTHER PUBLICATIONS

Rios et al, J. Am. Chem. Soc., 1996, 118, 11313-11314.*

* cited by examiner

*Primary Examiner* — Shailendra Kumar
(74) *Attorney, Agent, or Firm* — Hoglund & Pamias, PSC; Roberto J. Rios

(57) ABSTRACT

The use of quaternary halogenated ammonium salts for treating leishmaniasis infections and other parasitic diseases is described. Although there have been previous reports in which quaternary ammonium salts are used as antimalarial, antifungal, and antileishmanial compounds, the use of such salts containing a halogenated N-methyl substituent as a therapeutic agent against leishmaniasis had not been reported. The compounds described here, in specific those with a terminal arylalkenyl or diarylalkenyl moiety, are shown to inhibit the growth of *Leishmania panamensis* parasites, a known causative agent of leishmaniasis disease. In addition, the series of compounds are also extensive against malaria, Chagas disease, toxoplasmosis, and other parasitic diseases.

12 Claims, 7 Drawing Sheets

Reactants and conditions: a. (i) PhMgBr (2.6 equivalents)/dry ether; (ii) NH₄Cl; (iii) TsOH.  b. Aqueous 40% (CH₃)₂NH/THF.  c. ICH₂X/MeCN

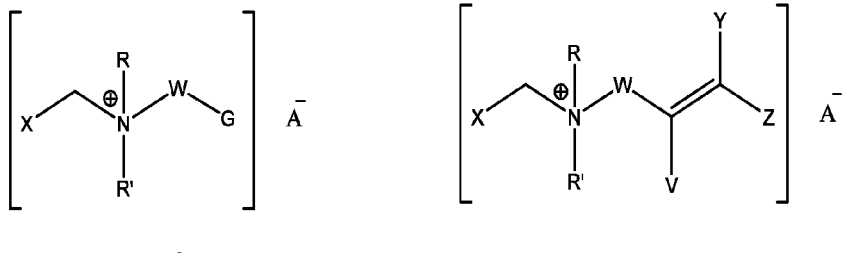

Compound 1: A⁻ = BF₄⁻; X = I; R = R' = CH₃; W = (CH₂)₃; G = CH₃
Compound 3: A⁻ = BF₄⁻; X = I; R = R' = CH₃; W = (CH₂)₃; V = H; Y = Z = C₆H₅
Compound 4: A⁻ = BF₄⁻; X = I; R = R' = CH₃; W = (CH₂)₃, V = H; Y = H; Z = C₆H₅ (E/Z stereoisomers mixture)
Compound 6: A⁻ = BF₄⁻; X = I; R = R' = CH₃; W = (CH₂)₃, V = H; Y = H; Z = p-C₆H₄OCH₃ (E/Z stereoisomers mixture)
Compound 7: A⁻ = BF₄⁻; X = I; R = R' = CH₃; W = (CH₂)₃, V = H; Y = H; Z = p-C₆H₄Cl (E/Z stereoisomers mixture)
Compound 8: A⁻ = BF₄⁻; X = I; R = R' = CH₃; W = (CH₂)₃, V = H; Y = H; Z = p-C₆H₄CF₃ (E/Z stereoisomers mixture)
Compound 9: A⁻ = BF₄⁻; X = I; R = R' = CH₃; W = (CH₂)₃, V = H; Y = H; Z = p-C₆H₄CH₃ (E/Z stereoisomers mixture)
Compound 10: A⁻ = Br⁻; X = Br; R = R' = CH₃; W = (CH₂)₂; V = Y = Z = H
Compound 11: A⁻ = BF₄⁻, X = Br, R = R' = CH₃, W = (CH₂)₂, V = H, Y = H; Z = C₆H₅ (E/Z stereoisomers mixture)

FIGURE 4

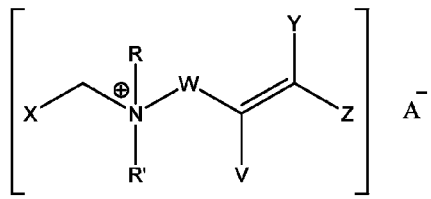

| | | | | | | | | 12 : G = OH |
|---|---|---|---|---|---|---|---|---|
| | | | | | | | | 3, 13, 14 : G = (structure with V, Y, Z) |

| Compound | A⁻ | X | R | R' | W | V | Y | Z | Ec₅₀ (µg/mL)<br>Ec₅₀ (µM) |
|---|---|---|---|---|---|---|---|---|---|
| 3a | I⁻ | I | CH₃ | CH₃ | (CH₂)₃ | H | C₆H₅ | C₆H₅ | 36.9<br>19.7 ± 1.5 |
| 3b | I⁻ | Cl | CH₃ | CH₃ | (CH₂)₃ | H | C₆H₅ | C₆H₅ | 127.4<br>56.3 ± 3.67 |
| 3c | I⁻ | H | CH₃ | CH₃ | (CH₂)₃ | H | C₆H₅ | C₆H₅ | 62.6<br>25.5 ± 0.6 |
| 13a | I⁻ | I | CH₃ | CH₃ | (CH₂)₂ | H | C₆H₅ | C₆H₅ | 69.7<br>36.2 ± 0.1 |
| 13b | I⁻ | Cl | CH₃ | CH₃ | (CH₂)₂ | H | C₆H₅ | C₆H₅ | 81.8<br>35.0 ± 5.7 |
| 13c | I⁻ | H | CH₃ | CH₃ | (CH₂)₂ | H | C₆H₅ | C₆H₅ | 64.8<br>25.5 ± 0.7 |
| 14a | I⁻ | I | CH₃ | CH₃ | (CH₂)₄ | H | C₆H₅ | C₆H₅ | 25.6<br>14.0 ± 0.9 |
| 14b | I⁻ | Cl | CH₃ | CH₃ | (CH₂)₄ | H | C₆H₅ | C₆H₅ | 89<br>40.5 ± 3.3 |
| 14c | I⁻ | H | CH₃ | CH₃ | (CH₂)₄ | H | C₆H₅ | C₆H₅ | 80.9<br>34.1 ± 5.1 |
| 12a | I⁻ | I | CH₃ | CH₃ | (CH₂)₂ | | | | 54.9<br>19.6 ± 1.8 |
| 12b | I⁻ | Cl | CH₃ | CH₃ | (CH₂)₂ | | | | 91.5<br>24.3 ± 1.3 |
| 12c | I⁻ | H | CH₃ | CH₃ | (CH₂)₂ | | | | 205<br>47.2 ± 7.1 |

FIGURE 7

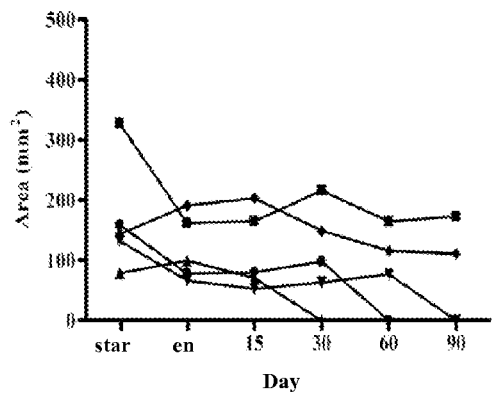
a. Topical treatment with compound 3b (3.91 mg/Kg/day for 10 days)
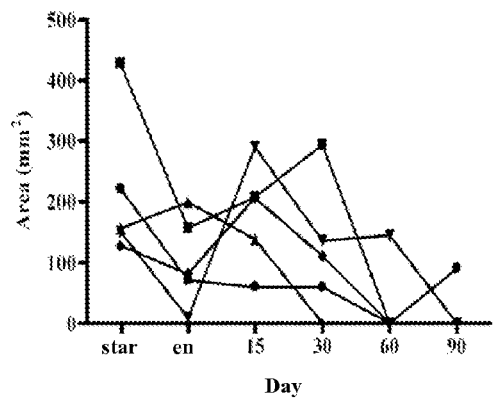
b. Topical treatment with compound 13b (1.99 mg/Kg/day for 10 days)
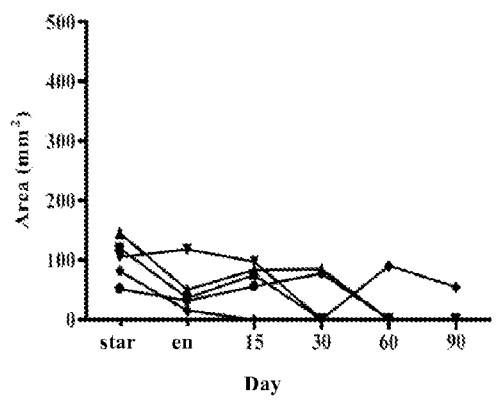
c. Topical treatment with 14c (1.28 mg/Kg/day for 10 days)
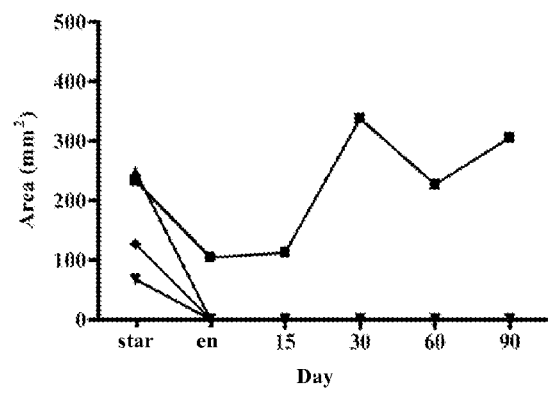
d. Intramuscular injection treatment with meglumine antimoniate (120 mg/Kg/day for 10 days)
FIGURE 9

QUATERNARY N-(HALOMETHYL) AMMONIUM SALTS AS THERAPEUTIC AGENTS

FIELD OF THE INVENTION

This invention relates to the field of biochemistry and to quaternary ammonium salts containing an N-(halomethyl) substituent as a therapeutic agent against leishmaniasis and Chagas disease. Leishmaniasis and Chagas disease are a group of diseases caused by trypanosomal parasites.

BACKGROUND OF THE INVENTION

There are three main clinical manifestations of leishmaniasis, which are currently classified as visceral, mucocutaneous, and cutaneous. The clinical form of leishmaniasis is determined by the *Leishmania* species, geographical location, and immune response of the host. The leishmaniasis diseases are endemic in 97 countries over 4 continents, frequently with one type being more of a threat over the other two in specific regions. It is estimated that more than 12 million people are affected worldwide, with 2 million new cases reported per year (1.5 million CL and 0.5 million VL).

On the other hands Chagas disease, also known as American trypanosomiasis, is a potentially life-threatening illness caused by the protozoan parasite, *Trypanosoma cruzi* (*T. cruzi*). It is found mainly in Latin America, where it is mostly transmitted to humans by the faeces of triatomine bugs.

An estimated 10 million people are infected worldwide, mostly in Latin America where Chagas disease is endemic. More than 25 million people are at risk of the disease. It is estimated that in 2008 Chagas disease killed more than 10,000 people.

The classification system divides the genus *Leishmania* into two sub-genera: *Leishmania* (*L*) *sensustricto*, present in both Old and New World, and *Viannia* (*V*), restricted to the New World. Within these two sub-genera, various species complexes have been individualized. Currently, at least twenty different species are recognized as human infectants. The most prevalent species involved in human cases of leishmaniasis are *L.* (*L*) *donovani, L.* (*L*) *infantum, L.* (*L*) *mexicana, L.* (*L*) *amazonensis, L.* (*L*) *tropica, L.* (*L*) *major, L.* (*L*) *aethiopica, L.* (*V*) *braziliensis, L.* (*V*) *guyanensis, L.* (*V*) *panamensis* and *L.* (*V*) *peruviana*. Each of these species is found in different locations worldwide and is responsible for causing different types of leishmaniasis.

Visceral leishmaniasis is the most pathogenic of the three types. It is caused by species of *L.* (*L*) *donovani* complex and *L.* (*L*) *infantum*. The common symptoms include irregular fever, weight loss, swelling of the spleen and liver and anemia. If left untreated, visceral leishmaniasis will lead to death. Endemic *L.* (*L*) *infantum* visceral leishmaniasis affects mainly children and *L.* (*L*) *donovani* VL affects people of any age group living in urban and rural areas. The onset of this type is usually abrupt, but symptoms may appear beginning 3 weeks to 2 years after exposure. With epidemic visceral leishmaniasis, all age groups are equally susceptible. With this type, males are also more likely to be infected than females at a ratio of 4:3. At this time, there is little understanding of the mechanisms by which apparent selectivity of hosts and effects are carried out.

Most research to treat leishmaniasis is focused on the development of improved chemotherapies because current drugs are unsatisfactory. Pentavalent antimonials, such as meglumine antimoniate and sodium stibogluconate are the most used anti-leishmanial drugs. While they can be therapeutic, they have unsatisfactory side effects such as systemic toxicity (cardiac, renal and hepatic), chemical pancreatitis, decreases in RBCs (Red Blood Cell Count), WBCs (White Blood Cell Count) and platelet counts and reversible peripheral neuropathy. Additionally, these drugs require prolonged treatment. The treatment with antimonials includes repeated [daily intramuscular or intravenous] injections for 20-28 days, requiring medical supervision. It is recommended that 20 mg/kg body weight be injected daily over that period of time. In addition to these drawbacks, *Leishmania* parasites are also becoming increasingly resistant to these treatments.

Amphotericin B is a secondary treatment used for leishmaniasis, especially when antimonial treatment has not been effective. This treatment is parenteral in nature and also highly toxic. It was found, however, that a total dose of 15 mg/kg body weight is 100% effective and a dose of 5-10 mg/kg is 90% effective against the Indian visceral disease. A liposomal formulation reduces the toxicity, but at a higher cost.

Other currently used drugs include the alkyl-glycero-phosphocholine, miltefosine, pentamidine and ketoconazole. Miltefosine is the first oral medication approved against leishmaniasis. Miltefosine commonly induces gastrointestinal side-effects such as anorexia, nausea, vomiting (38%) and diarrhea (20%). Most episodes are brief and resolve as treatment is continued. Occasionally, the side-effects can be severe and require interruption of treatment. Skin allergy, elevated hepatic transaminase concentrations and, rarely, renal insufficiency may be observed. Miltefosine should be taken after meals, and, if multiple doses are to be taken, they should be divided. Miltefosine is potentially teratogenic and should not be used by pregnant women or women with childbearing potential for whom adequate contraception cannot be assured for the duration of treatment and for 3 months afterwards.

Ketokonazole have variable efficacy in leishmaniasis treatment. Pentamidine is given intramuscularly or, preferably, by intravenous infusion. Severe adverse effects—diabetes mellitus, severe hypoglycaemia, shock, myocarditis and renal toxicity—limit its use.

New drugs such as paromomycin (aminosidine), an aminoglycoside antibiotic, usually administered intramuscularly, are under study. The 15 mg/kg sulfate is equivalent to 11 mg/kg of base, and the 20 mg/kg sulfate is equivalent to 15 mg/kg of base. Mild pain at the injection site is the commonest adverse event (55%). Reversible ototoxicity occurs in 2% of patients. Renal toxicity is rare. Some patients may develop hepatotoxicity, indicated by raised hepatic enzyme concentrations; tetany has also been reported.

Quaternary ammonium compounds such as octadecyltrimethyl ammonium bromide and dodecyltrimethyl ammonium bromide have also been reported to inhibit the growth of *L. major* promastigotes. The use of alkyl quaternary ammonium compounds including certain choline analogs for treating or preventing fungal and trypanosomal (e.g., Leishmaniasis) infections is also known.

The compounds seem to inhibit or perturb choline transport into the parasites, thus inhibiting parasites growth. Other quaternary ammonium salts that are known antibacterials, such as methylbenzethonium chloride, benzethonium chloride, cetalkonium chloride, benzalkonium chloride, and cetrimonium bromide have been used in combination with other drugs such as paromomycin and meglumine antimoniate; as a well as benzethonium chloride, in combination with other drugs such as hexadecyl-phosphorylcholine.

Chagas disease can be treated with either benznidazole or nifurtimox. Both medicines are almost 100% effective in curing the disease if given soon after infection at the onset of the acute phase. However, the efficacy of both diminishes the longer a person has been infected. Benznidazole and nifurtimox should not be taken by pregnant women or by people with kidney or liver failure. Nifurtimox is also contraindicated for people with a background of neurological or psychiatric disorders.

Multiple metabolic pathways and specific molecular targets have been studied in trypanosomatid parasites. Membrane lipid biosynthesis pathways are a viable target for antitrypanosomal compounds since phospholipids have an important role in the cell biology of the parasite and membrane lipid composition differs significantly when compared to mammals.

SUMMARY OF THE INVENTION

The present invention presents a series of quaternary N-(halomethyl) ammonium salts with general structure $[XCH_2—N^+(R)(R')—W—G]A^-$, of facile synthesis and at a low cost of production.

According to an aspect of the invention, in vitro and in vivo studies proved the efficacy of some of the evaluated compounds against cutaneous leishmaniasis and other parasitic diseases.

According to another aspect of the invention, compounds 3b, 3c, 13a, 13b, 13c, 14a, 14b and 14c were synthesized for the first time according to FIG. 4.

BRIEF DESCRIPTION OF THE DRAWINGS

Further features and advantages of the invention will become apparent from the following detailed description taken in conjunction with the accompanying figures showing illustrative embodiments of the invention, in which:

FIG. 4. Show the compounds tested in vitro against L. tarentolae.

FIG. 5. Show the compounds evaluated against infected macrophage cells with L. (V) panamensis.

FIG. 7. Show the table 1, the in vitro effectiveness of compounds (EC50) against axenic amastigotes of L. (V) panamensis.

FIG. 9. Show the reduction of the cutaneous leishmaniasis lesion area (mm2) of infected golden hamsters as a function of time (days) after topical treatment.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
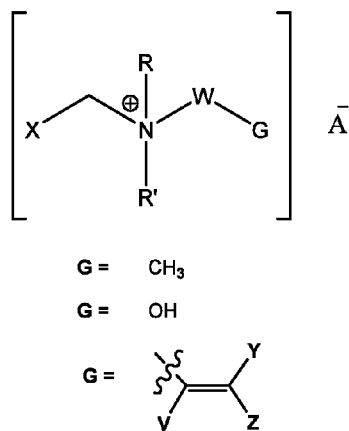
FIG. 1 illustrates the general chemical structure of the series of quaternary N-(halomethyl) ammonium salts.

FIG. 1 illustrates the general chemical structure of the series of quaternary N-(halomethyl) ammonium salts according to the invention. Anion $A^-$ is a halide (chloride, bromide, iodide), acetate, p-toluenesulfonate or any other pharmaceutically acceptable anion. R and R' are alkyl groups such as methyl, ethyl, propyl or butyl (they are either the same group or different from each other). W is a chemical tether, characterized by a carbon chain $(CH_2)_n$ constituted by a number n of methylene units such that n=1, 3, 4, 5, 6, 7, 8, 9, 10, 11, 12, 13, 14; the structure of the chemical tether W either a normal or a branched hydrocarbon chain.

W is also a chemical tether constituted by an oxycarbonated chain with structure represented by $—(CH_2)_s[(CH_2)_2—O—]_t(CH_2)_u—$, made of a number s of methylene units such that s=0, 1, 2, 3, 4, 5, 6, 7, 8, 9, 10, and a number t of ethyleneoxy units such that t=0, 1, 2, 3, 4, 5, 6, 7, 8, 9, 10, and a number of u methylene units such that u=0, 1, 2, 3, 4, 5, 6, 7, 8, 9, 10. In addition, W is also a chemical tether constituted by a chain with structure $(CH_2)_p[—O—Si(CH_3)_2]_q—O—CH_2)_r—$ made of a number p of methylene units such that p=1, 2, 3, 4, and a number q of dimethylsiloxane units such that q=0, 1, 2, 3, 4, 5, 6, 7, 8, 9, 10, and a number of r methylene units such that r=0, 1, 2, 3, 4, 5, 6, 7, 8, 9, 10.

The tail G is a methyl group, a hydroxyl group, or an alkenyl system with groups V, Y and Z attached to the vinylic carbons. V, Y and Z are either the same group or they are different from each other when G is an alkenyl system. Substituents V and/or Y and/or Z correspond to hydrogen, phenyl group or any aromatic or heteroaromatic group, or any alkyl, alkenyl or alkynyl group. The aromatic or heteroaromatic group bears hydrogen atoms or any kind and number of substituents in any place of the ring, with the aromatic substituents including hydroxyl, methoxy or any alkoxy group, O-acetyloxy or any O-acyloxy group, amino, N-acetylamino or any N-acylamino group, fluorine, chlorine, bromine, iodine, α,α,α-trifluoromethyl, any alkyl substituent, or any other pharmaceutically acceptable substituent and any substitution pattern, with a total number of substituents in the ring being zero, one, two, three, four, five or six. These substituents may also be chemically connected with some others generating additional annular patterns.

According to FIG. 1, the screening revealed that compounds inhibit the growth of parasites, even though they work out with different capacities.

QUATERNARY N-(HALOMETHYL) AMMONIUM SALTS AS THERAPEUTIC AGENTS, is a series of compounds that are characterized by a general structure consisting of a quaternary N-(halomethyl) ammonium cation head, a tail G, a chemical tether W, and a counter ion $A^-$. The counter ion $A^-$ is chloride ($Cl^-$), bromide ($Br^-$), iodide ($I^-$), acetate ($CH_3COO^-$), tosylate ($p-CH_3C_6H_4SO_3^-$), or any other pharmaceutically acceptable anion. The quaternary N-(halomethyl) ammonium cation head is constituted by a nitrogen atom which is coordinated to four ligands with the following specific description: (i) a halomethyl group ($CH_2—X$) where the halogen X is fluorine (F), chlorine (Cl), bromine (Br) or iodine (I); (ii) an alkyl group R, such as methyl, ethyl, n-propyl or n-butyl; (iii) another alkyl group R', such as methyl, ethyl, n-propyl or n-butyl; (iv) a chemical tether W which joins the quaternary nitrogen head to the tail G.

The tail G is a methyl group, a hydroxyl group, or an alkenyl system with groups V, Y and Z attached to the vinylic carbons. V, Y and Z are either the same group or different from each other when G is an alkenyl system. Substituents V and/or Y and/or Z correspond to hydrogen, phenyl group or any aromatic or heteroaromatic group, or any alkyl, alkenyl or alkynyl group. The aromatic or heteroaromatic group bears hydrogen atoms or any kind and number of substituents in any place of the ring, with the aromatic substituents including hydroxyl, methoxy or any alkoxy group, O-acetyloxy or any O-acyloxy group, amino, N-acetylamino or any N-acylamino group, fluorine, chlorine, bromine, iodine, α,α,α-trifluoromethyl, any alkyl substituent, or any other pharmaceutically acceptable substituent and any substitution pattern, with a total number of substituents in the ring being zero, one, two, three, four, five or six. These substituents may also be chemically connected with some others generating additional annular patterns.

The chemical tether W is a carbon chain $(CH_2)_n$ constituted by a number n of methylene units such that n=1, 2, 3, 4, 5, 9, 10, 11, 12, 13, 14. This chemical tether W could also be a branched hydrocarbon chain.

QUATERNARY N-(HALOMETHYL) AMMONIUM SALTS AS THERAPEUTIC AGENTS with a chemical tether W is characterized by a chain with structure $—(CH_2)_p[—O—Si(CH_3)_2]_q—O—(CH_2)_r—$ made of a number p of methylene units such that p=1, 2, 3, 4, and a number q of dimethylsiloxane units such that q=0, 1, 2, 3, 4, 5, 6, 7, 8, 9, 10, and a number of r methylene units such that r=0, 1, 2, 3, 4, 5, 6, 7, 8, 9, 10.

Also, the chemical tether W is characterized by an oxycarbonated chain with structure represented by $—(CH_2)_s[(CH_2)_2—O-]_t(CH_2)_u—$, made of a number s of methylene units such that s=0, 1, 2, 3, 4, 5, 6, 7, 8, 9, 10, and a number t of ethyleneoxy units such that t=0, 1, 2, 3, 4, 5, 6, 7, 8, 9, 10, and a number of u methylene units such that u=0, 1, 2, 3, 4, 5, 6, 7, 8, 9, 10.

QUATERNARY N-(HALOMETHYL) AMMONIUM SALTS AS THERAPEUTIC AGENTS are effective against *Leishmania tarentolae* parasites, non-pathogenic species that are used for pre-screening processes in the promastigote stage.

Some of the QUATERNARY N-(HALOMETHYL) AMMONIUM SALTS AS THERAPEUTIC AGENTS are effective against axenic *L. (V) panamensis* and *L. (L) amazonensis* parasites, human pathogenic species that causes cutaneous and mucocutaneous leishmaniasis.

Also, some of the QUATERNARY N-(HALOMETHYL) AMMONIUM SALTS AS THERAPEUTIC AGENTS are effective against *L. (V) panamensis* and *L. (L) amazonensis* parasites, in the amastigote stage that have infected macrophage cells.

QUATERNARY N-(HALOMETHYL) AMMONIUM SALTS AS THERAPEUTIC AGENTS is a series of compounds that inhibit the growth of parasites, even though they work out with different capacities. Those compounds with a terminal arylalkenyl or diarylalkenyl (i.e. G=alkenyl system with V=H, Y=H, Z=$C_6H_5$ or V=H, Y=$C_6H_5$, Z=H or V=H, Y=$C_6H_5$, Z=$C_6H_5$) were more effective against the parasites than those without this moiety. Interestingly, compounds with G being a terminal diarylalkenyl moiety (i.e. V=H, Y=$C_6H_5$, Z=$C_6H_5$) are the most effective.

The use of QUATERNARY N-(HALOMETHYL) AMMONIUM SALTS AS THERAPEUTIC AGENTS for a topical treatment of cutaneous leishmaniasis on infected golden hamsters led to 100% healing of the lesion after three months of treatment.

The invention originates from the study of the effect of some quaternary N-(halomethyl) ammonium salts on the in vitro viability of *L. tarentolae* parasites. In consideration of the structural similarity of this salts and choline, it was hypothesized that quaternary N-(halomethyl) ammonium salts should have an effect on the choline transport and metabolic role in the formation of the parasite membrane, resulting in consequence in a possible active ingredient for a pharmaceutical composition against trypanosomal parasites. So, compounds shown in FIG. 4 were tested for their in vitro efficacy against *L. tarentolae* parasites (a non-pathogenic species) in the promastigote stage.

The screening revealed that compounds inhibit the growth of parasites, even though they work out with different capacities. Of all these tested compounds FIG. 4 the compounds with a terminal arylalkenyl moiety (compounds 4, 6-9, 11) or diarylalkenyl moiety (compound 3) were more effective against the parasites than those without this moiety (compound 1). Interestingly, compound 3, having a terminal diarylalkenyl moiety is the most effective.

Figure 2:
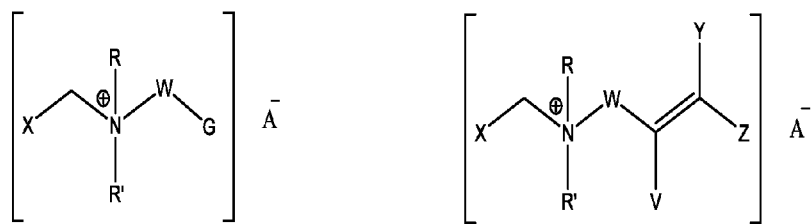
FIG. 2. Describe the compounds synthesized and evaluated against axenic amastigotes of L. (V) panamensis. Compounds 3b, 13b and 14c were also evaluated in vivo as a topical treatment.

Then, a series of compounds analogous to compound 3 (characterized by a tail G being a diarylalkenyl moiety) were synthesized in order to assess their in vitro effectiveness against *L. (V) panamensis*, a pathogenic species which causes human mucocutaneous leishmaniasis. Other halogenated analogs of choline were also synthesized and included in this in vitro effectiveness study. FIG. 2 illustrates the compounds evaluated for their in vitro effectiveness against axenic amastigotes of *L. (V) panamensis*.

Given that *Leishmania* parasites are known to infect monocyte cells, mostly macrophages and neutrophils, the in vitro effectiveness of some of the compounds was also tested on *L. (V) panamensis* in the amastigote stage that have been set to infect macrophage cells. FIG. 5 contains the list of compounds evaluated.

Figure 6:
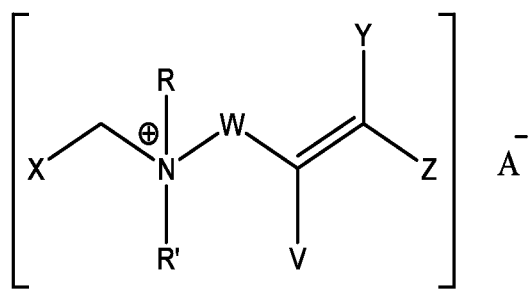
FIG. 6. Show the compounds evaluated in the in vivo study on golden hamster for cutaneous leishmaniasis.

It was decided then to carry out a preliminary in vivo animal study according to standard practices using the golden hamster model for cutaneous leishmaniasis, using the compounds with the better profile as therapeutic agents against leishmaniasis. For that purpose the in vivo effectiveness of compounds 3b, 13b and 14c were tested FIG. 6.

Results

The table shown in FIG. 7 contains the $EC_{50}$ values (molar amount of compound that kills 50% of parasites in sample) obtained against axenic amastigotes of *L. (V) panamensis*. QUATERNARY N-(HALOMETHYL) AMMONIUM SALTS AS THERAPEUTIC AGENTS were compared with the respective non-halogenated (i.e. N,N,N-trimethyl quaternary ammonium salts) and with two compounds commonly used to treat leishmaniasis (meglumine antimoniate and amphotericin B).

As shown in FIG. 7 compound 14a is the most effective of them, being more efficient than compound 3a. The $EC_{50}$ values for meglumine antimoniate and amphotericin B are 312±18.6 μM and 0.041±0.001 μM respectively.

Figure 8:
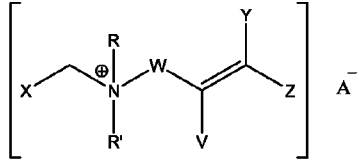
FIG. 8. Show the table 2, the in vitro effectiveness of compounds (EC50) against amastigotes of L. (V) panamensis that have infected macrophage cells.

On the other hand, the results of the in vitro activity study of some QUATERNARY N-(HALOMETHYL) AMMONIUM SALTS AS THERAPEUTIC AGENTS shown in FIG. 5 against infected macrophage cells with *Leishmania panamesis* are shown in FIG. 8.

The $EC_{50}$ values for meglumine antimoniate and amphotericin B are 6.33±0.86 μg/mL and 0.05±0.001 μg/mL respectively.

It was decided then to carry out a small in vivo animal study according to standard practices using the golden hamster model for cutaneous leishmaniasis. For that purpose the in vivo effectiveness of compounds 3b, 13b and 14c were tested. Treatment consisted of a topical application of the compound suspended in an aqueous buffer (neutral pH) daily for ten days.

The results are summarized in FIG. 9 (*a-d*) and evidence that application of the compounds topically is conductive to the cure of the majority of the animals in the study, with similar results to those found when using meglumine antimoniate via intramuscular injection. The required dosage of compounds 3b, 13b, and 14c is smaller than that of meglumine antimoniate.

Some additional studies show that the compounds induce parasites death via an apoptotic mechanism. An understanding of the mechanism of parasite's death is of importance in the future development of compounds that are better against the parasites. Choline is a quaternary ammonium salt that is necessary for the construction of cell membranes. Choline is used by cells to biosynthesize phosphatidyl choline, one of the primary phospholipids that constitute cellular membranes. Given the similarity between the compounds tested and choline (see Compound 12c in FIG. 7, it was hypothesized that the compounds of the invention may inhibit the uptake of choline by the parasites, or that they may inhibit some enzymes which are catalyzing the transformation of choline.

Phosphatidyl choline can be synthesized by the parasite following the traditional Kennedy pathway (Zhang and Beverley, 2010), in which choline is converted to phosphatidyl choline via a sequence of steps, each catalyzed by a specific enzyme. The first step involves the phosphorylation of choline with the enzyme choline kinase. Kinetic studies using the choline kinase of $L.$ $(L)$ $infantum$ reveal that some of the compounds, especially compound 14a is able to inhibit this enzyme, lowering its catalytic efficiency. Other studies reveal that some of the compounds with Structure 1, especially compound 14a, interferes with the in vitro uptake of choline by promastigotes of $L.$ $tarentolae$ and, also inhibits the in vitro production of phosphatidyl choline by these parasites According to an embodiment of the invention, a daily topical application of a composition based on the quaternary N-(halomethyl) ammonium salts in an aqueous buffer solution (neutral pH) is proposed.

Figure 3:
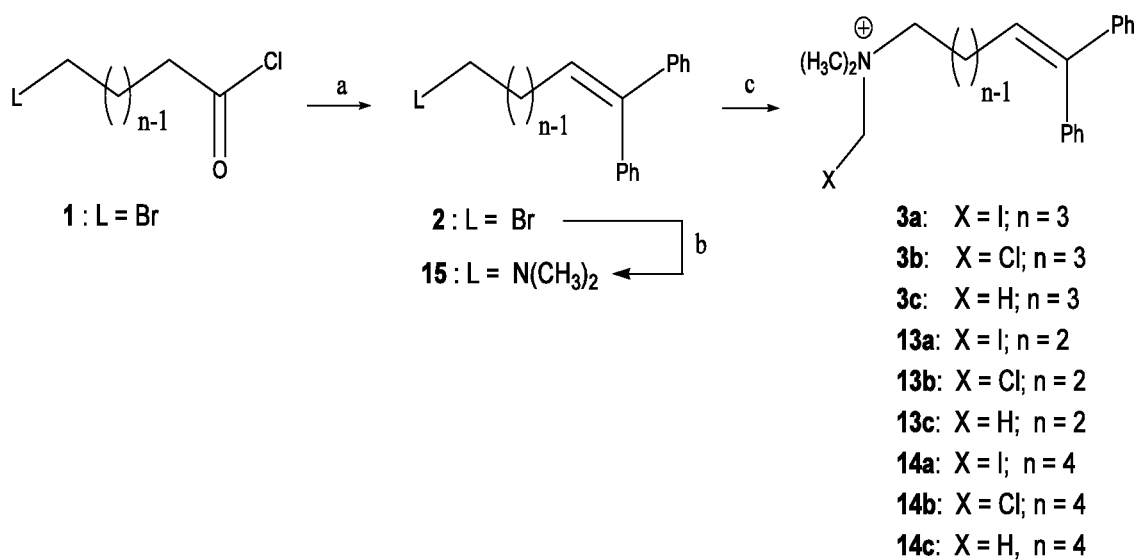
FIG. 3. Show the four-step synthetic scheme for producing the quaternary N-(halomethyl) ammonium salts.

The syntheses of some representative quaternary N-(halomethyl) ammonium salts are accomplished according to standard procedures, FIG. 3.

The starting materials for this three-step sequence are ω-bromoacyl chlorides 1 which are converted into ω-bromo-α,α-diphenyl-α-alkenes 2 via a Grignard reaction with excess of phenylmagnesium bromide and the further dehydration of the resulting tertiary ω-bromo-α,α-diphenyl-carbinols with p-toluenesulfonic acid. Then, bromide anion is displaced by dimethylamine affording the respective tertiary amine 15, which is in turn made to react with diiodomethane or chloroiodomethane giving rise to the target quaternary N-(halomethyl) ammonium salts 3, 13 or 14.

In a typical run, 2.6 equivalents of phenyl magnesium bromide are added to 1.0 equivalent of 5-bromopentanoyl chloride dissolved in dried diethyl ether under inert atmosphere at 0° C. and stirred during 15 minutes. After this time the mixture is warmed up to room temperature, and then ammonium chloride is added slowly to the mixture, and worked up in the usual manner to produce 5-bromo-1,1-diphenyl-1-pentanol as a white solid. The crude product is then refluxed during 6 hours with p-toluenesulfonic acid (ratio 60:1) under benzene, and worked up in the usual manner to yield 5-bromo-1,1-diphenyl-1-pentene as a yellow oil.

Next, an aqueous solution (40%) of dimethyl amine (25 equivalents) is added slowly to a THF solution of 1.0 equivalent of 5-bromo-1,1-diphenyl-1-pentene that has been obtained in the previous step. The mixture is then stirred at room temperature for 24 hours, and worked up in the usual manner to yield 5-(N,N-dimethyl)amino-1,1-diphenyl-1-pentene as a yellow oil.

Finally, 1.0 equivalent of the resulting amine is mixed with 4.0 equivalents of diiodomethane in acetonitrile. The mixture is stirred for 20 hours or until the quaternary N-(halomethyl) ammonium salt precipitates as a white solid. The product is then recrystallized from hot water.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A compound with therapeutic activity against $Leishmania$ parasites, having the formula:

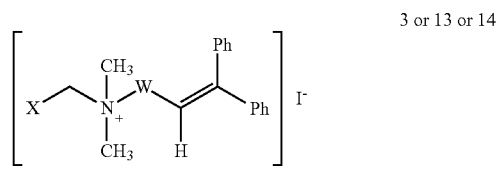

3 or 13 or 14 wherein:
X=Cl or I; and
W=(CH$_2$)$_3$, (CH$_2$)$_2$ or (CH$_2$)$_4$.

2. The compound of claim 1, having the formula:

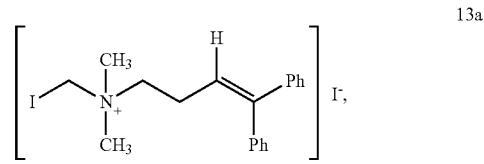

13a wherein said compound is effective against axenic $L.$ $(V)$ $panamensis$ and $L.$ $(L)$ $amazonensis$ parasites, human pathogenic species that causes cutaneous and mucocutaneous leishmaniasis.

3. The compound of claim 1, having the formula:

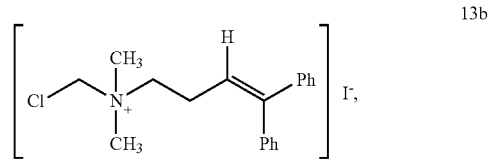

13b wherein said compound is effective against axenic $L.$ $(V)$ $panamensis$ and $L.$ $(L)$ $amazonensis$ parasites, human pathogenic species that causes cutaneous and mucocutaneous leishmaniasis.

4. The compound of claim 1, having the formula:

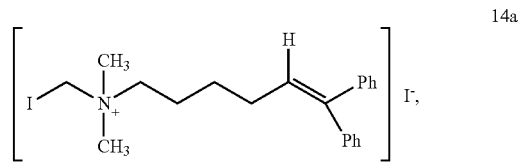

14a wherein said compound is effective against axenic *L. (V) panamensis* and *L. (L) amazonensis* parasites, human pathogenic species that causes cutaneous and mucocutaneous leishmaniasis.

5. The compound of claim 1, having the formula:

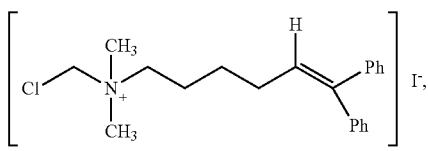

14b wherein said compound is effective against axenic *L. (V) panamensis* and *L. (L) amazonensis* parasites, human pathogenic species that causes cutaneous and mucocutaneous leishmaniasis.

6. The compound of claim 4, wherein the compound inhibits the enzyme choline kinase of *L. (L) infantum* and lowers its catalytic efficiency.

7. The compound of claim 4, wherein the compound interferes with an in vitro uptake of choline by promastigotes of *L. tarentolae* and also inhibits the in vitro production of phosphatidyl choline by parasites.

8. A method of treatment of cutaneous Leishmaniasis comprising cutaneous application of the compound according to claim 1.

9. A compound with antileishmanial pharmaceutical activity, having a quaternary N-(halomethyl) ammonium cation head, a tail G, a chemical tether W, and a counter ion A-, with the Formula I:

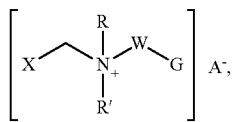

I wherein:

X=Cl or I or Br or F;

R and R'=$CH_3$ or $CH_3CH_2$ or $CH_3CH_2CH_2$ or $CH_3CH_2CH_2CH_2$;

A$^-$=Cl— or Br— or I— or $CH_3COO$— or p-$CH_3C_6H_4SO_3^-$ or any other pharmaceutically acceptable anion;

the tail G is a methyl group or a hydroxyl group or an alkenyl system with structure C(V)=C(Y)(Z) where V, Y and Z correspond to hydrogen or phenyl group or any alkyl or alkenyl or alkynyl group or any aromatic or heteroaromatic group, where the aromatic or heteroaromatic group bears hydrogen atoms or any kind and number of substituents in any place of the ring, with the aromatic substituents including hydroxyl, methoxy or any alkoxy group, O-acetyloxy or any O-acyloxy group, amino, N-acetylamino or any N-acylamino group, fluorine, chlorine, bromine, iodine, α,α,α-trifluoromethyl, any alkyl substituent, or any other pharmaceutically acceptable substituent and any substitution pattern, with a total number of substituents in the ring being zero, one, two, three, four, five or six; these substituents may also be chemically connected with some others generating additional annular patterns; and the tether W is a carbon chain $(CH_2)_n$, constituted by a number n of methylene units such that n=1, 2, 3, 4, 5, 6, 7, 8, 9, 10, 11, 12, 13, 14 or a branched hydrocarbon chain.

10. The compound of claim 9, wherein the tail G is an alkenyl system having structure C(V)=C(Y)(Z) with one of: V=H, Y=H, Z=$C_6H_5$ or V=H, Y=$C_6H_5$, Z=H or V=H, Y=$C_6H_5$, Z=$C_6H_5$.

11. The compounds of claim 9, wherein said compounds inhibit the growth of parasites related to Leishmaniasis disease, malaria, Chagas disease, and toxoplasmosis.

12. The compound of claim 9, wherein said compound has therapeutic activity against *Leishmania* parasites.

* * * * *